United States Patent
Whitcup

(10) Patent No.: US 9,314,425 B2
(45) Date of Patent: Apr. 19, 2016

(54) OPHTHALMIC COMPOSITIONS AND METHODS FOR TREATING OPHTHALMIC CONDITIONS

(71) Applicant: Allergan, Inc., Irvine, CA (US)

(72) Inventor: Scott M. Whitcup, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/598,818

(22) Filed: Jan. 16, 2015

(65) Prior Publication Data

US 2015/0133415 A1 May 14, 2015

Related U.S. Application Data

(60) Continuation of application No. 13/236,432, filed on Sep. 19, 2011, now abandoned, which is a division of application No. 11/180,752, filed on Jul. 11, 2005, now abandoned.

(60) Provisional application No. 60/587,092, filed on Jul. 12, 2004.

(51) Int. Cl.

| | |
|---|---|
| *A61K 31/56* | (2006.01) |
| *A61K 31/57* | (2006.01) |
| *A61K 47/38* | (2006.01) |
| *A61K 9/00* | (2006.01) |
| *A61K 31/44* | (2006.01) |
| *A61K 31/573* | (2006.01) |
| *A61K 47/34* | (2006.01) |
| *A61K 31/575* | (2006.01) |
| *A61K 31/58* | (2006.01) |

(52) U.S. Cl.
CPC .............. *A61K 9/0024* (2013.01); *A61K 9/0048* (2013.01); *A61K 9/0051* (2013.01); *A61K 31/44* (2013.01); *A61K 31/56* (2013.01); *A61K 31/57* (2013.01); *A61K 31/573* (2013.01); *A61K 31/575* (2013.01); *A61K 31/58* (2013.01); *A61K 47/34* (2013.01); *A61K 47/38* (2013.01); *Y10S 514/912* (2013.01)

(58) Field of Classification Search
None
See application file for complete search history.

(56) References Cited

U.S. PATENT DOCUMENTS 6,136,334 A * 10/2000 Viegas et al. ................ 424/427

* cited by examiner

*Primary Examiner* — Gigi Huang

(74) *Attorney, Agent, or Firm* — Brigitte C. Phan; Ted A. Chan

(57) ABSTRACT

Compositions, and methods of using such compositions, useful for placement, for example injection, into the interior of human or animal eyes are provided. Such compositions include a therapeutic component, such as one or more corticosteroids, a biocompatible polymeric component, and a solvent component. The composition is in a fluid form before placement in the interior of an eye, and becomes less fluid after the composition is placed in the eye to form an extended or delayed release drug delivery element or system. The drug delivery element is formed by the dissipation of the solvent from the composition when the composition is placed in the interior of an eye. One example of a composition includes triamcinolone acetonide as a therapeutic agent. A method of treating an ophthalmic condition, or otherwise improving or enhancing vision of a patient, comprises placing the fluid composition in the interior of the eye. The method may be practiced by injecting the fluid composition into the interior of the eye.

6 Claims, No Drawings

OPHTHALMIC COMPOSITIONS AND METHODS FOR TREATING OPHTHALMIC CONDITIONS

CROSS-REFERENCE TO RELATED APPLICATIONS

This is a continuation application to U.S. patent application Ser. No. 13/236,432, filed on Sep. 19, 2011, which is a divisional application of U.S. application Ser. No. 11/180,752, filed on Jul. 11, 2005, now abandoned, which claims benefit of U.S. Provisional Application Ser. No. 60/587,092, filed Jul. 12, 2004, the contents of which are hereby incorporated by reference in their entirety.

BACKGROUND

The present invention relates to ophthalmic compositions that are delivered to the interior of an eye of a human or animal. More particularly, the invention relates to ophthalmically acceptable compositions including one or more therapeutic agents. Such compositions are advantageously intraocularly placed into the interior of an eye and form solid or semi-solid drug delivery elements in situ that are effective in providing extended or delayed release of the therapeutic agent or agents into the eye.

Steroids, for example corticosteroids, among other agents, are utilized to treat a wide variety of ophthalmic diseases that affect the posterior segment of an eye. Examples of some diseases treated with corticosteroids include: central retinal vein occlusion (CRVO), branch retinal vein occlusion (BRVO), choroidal macular edema (CME), diabetic macular edema (DME), diabetic macular retinopathy, uveitis, telangitis, and age related macular degeneration (ARMD) as well as other diseases or conditions of the eye, for example of the posterior segment of the eye.

In treating ocular diseases or disorders, steroids can be administered systemically. However, systemic administration of steroids is often associated with side effects that are often too substantial for ophthalmic use. Thus, topical, suprachoroidal, subconjunctival, retrobulbar, and intravitreal administration have also been studied. These administration techniques typically employ aqueous compositions containing a steroid.

The desired site of action for therapeutic agents administered to the posterior segment of an eye generally, and corticosteroids in particular, is the retinal pigmented epithelium (RPE). The RPE is a single cell layer responsible for maintenance of the blood-retinal barrier as well as subretinal fluid volume and composition. The cells of the RPE comprise the outer blood retinal barrier and are joined by zonulae occludente tight junctions. As such, permeation of compounds into the RPE is quite limited. Thus, regardless of the administration route, penetration of a therapeutic agent through the outer blood-retinal barrier is limited. To overcome these limitations extremely high and potentially toxic doses of drugs are frequently used.

In certain situations, drugs are administered by controlled or sustained release technologies to attempt to increase their duration of action or reduce the toxicity of transient high general concentrations.

Some poorly soluble therapeutic agents, such as corticosteroids, however, are well tolerated locally and have a prolonged duration of action by virtue of their own intrinsic dissolution rates. For example, triamcinolone acetonide has been successfully administered by direct intravitreal injection in an aqueous composition due to its slow dissolution rate and tolerability. Unfortunately, side effects from the existing triamcinolone acetonide formulation often include endophthalmitis as well as retinal toxicity from the benzyl alcohol preservative. Glaucoma and cataract are also observed.

Reducing the lens concentration of a corticosteroid may help mitigate the cataractogenic potential of these drugs. Additionally, reducing the anterior segment concentration of the corticosteroids relative to the posterior concentrations may reduce the chance of elevating the TIGR (MYOC, GLC1A) gene activity in the trabecular meshwork thought to be associated with steroid induced glaucoma.

Some extended release compositions containing therapeutic agents have been described. For example, U.S. Pat. No. 5,077,049 discloses a biodegradable system for regenerating the periodontium. U.S. Pat. No. 5,324,519 discloses a biodegradable polymer composition. U.S. Pat. Nos. 5,487,897 and 6,395,293 disclose a biodegradable implant precursor. U.S. Pat. No. 5,702,716 discloses polymeric compositions useful as controlled release implants. U.S. Pat. No. 5,717,030 discloses an adjunctive polymer system for use with medical device. U.S. Pat. No. 5,780,044 discloses liquid delivery compositions. U.S. Pat. No. 6,143,314 discloses controlled release liquid delivery compositions with low initial drug burst. U.S. Pat. No. 6,261,583 discloses a moldable solid delivery system. U.S. Pat. No. 6,461,631 discloses a biodegradable polymer composition. U.S. Pat. No. 6,565,874 discloses polymeric delivery formulations of leuprolide with improved efficacy.

Thus, there is a need for new ophthalmic compositions for injection into the interior of eyes of humans or animals and methods for providing desired therapeutic effects of ophthalmic conditions of eyes of humans or animals.

SUMMARY OF THE INVENTION

New compositions and methods for treating ophthalmic conditions of eyes of humans or animals are provided. The present compositions are highly suitable for intraocular administration into the interior of an eye and provide therapeutic effects to the eye, which may be effective in stabilizing, enhancing or improving a patient's vision.

In one broad embodiment, an ophthalmic composition comprises a therapeutic component, a biocompatible polymeric component, and a solvent component. The solvent component is effective in maintaining the polymeric component in a fluid state. For example, the composition may be a liquid. The liquid may be a suspension or a solution, that is, the therapeutic component may be provided as particles in suspension, or the therapeutic component may be solubilized in a solution. The fluid composition when placed in the interior of an eye becomes less fluid and forms a solid or semi-solid drug delivery element, which is effective in releasing the therapeutic component for extended periods of time. The composition may be used in a method to enhance or improve vision of a patient by treating one or more ophthalmic conditions.

In one embodiment, a composition useful for intraocular placement in an eye of a human or animal comprises a corticosteroid component present in a therapeutically effective amount; a biocompatible polymeric component in an amount effective to delay release of the corticosteroid component into the interior of the eye after the composition is placed in the eye; and an ophthalmically compatible solvent component in an amount effective to solubilize the polymeric component.

The composition is effective, after being placed into the interior of the eye, to form a delayed release composition, such as a drug delivery element, effective to delay or extend the release of the corticosteriod component in the eye relative to intraocular placement of a substantially identical composition without the polymeric component.

Methods of treating patients are also disclosed and are included within the scope of the present invention. In general, such methods comprise placing or administering, e.g. injecting a liquid therapeutic agent-containing composition, for example, a composition in accordance with the present intention, into the interior of an eye of a human or animal. Such administering is effective in providing a desired therapeutic effect. The administering step advantageously comprises at least one of intravitreal injecting, subconjunctival injecting, sub-tenon injecting, retrobulbar injecting, suprachoroidal injecting and the like. The liquid composition forms a solid or semi-solid drug delivery element when the liquid composition is placed in the eye. The administration of the composition into the eye typically occurs without placing the composition in the cul-de-sac of the eye.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

These and other aspects and advantages of the present invention are apparent in the following detailed description, examples and claims.

DETAILED DESCRIPTION

The present invention involves compositions, such as ophthalmic compositions, that provide therapy to a patient. In accordance with the disclosure herein, compositions are disclosed that are useful for placement, preferably by injection, into the interior of an eye of a human or animal, and preferably a living human or animal. Such compositions are preferably administered into an eye of a patient in a fluid form, such as a liquid. By administering the compositions as a fluid, the administration may occur without forming an incision in the eye. The liquid composition becomes less fluid when placed in the eye, thereby forming an extended release drug delivery element. For example, the composition becomes a solid, a semi-solid, or a moldable drug-releasing element when placed in the eye. The element is effective in providing prolonged delivery of a therapeutic agent or agents to the eye, for example, to a posterior segment of the eye, or an anterior segment of the eye. The element is biodegraded and/or bioeroded as the implant element is releasing the therapeutic agent or agents. The components of the element are absorbed by the patient's body thereby reducing, and preferably eliminating, the need to surgically remove the element after the therapeutic agent or agents have been released.

In general, the present compositions comprise a therapeutic component, a biocompatible polymeric component, and an ophthalmically compatible solvent component. The composition is effective, after being placed into the interior of an eye of a patient, to form a delayed release composition, such as a drug delivery element, effective in delaying the release of the therapeutic component in the eye. The delay of release is relative to intraocular placement of a substantially identical composition without the polymeric component.

As used herein, a "therapeutic component" refers to a portion of the ophthalmic composition or a portion of the drug delivery element that is formed in the eye of a patient, which comprises one or more therapeutic agents or substances used to treat a medical ophthalmic disease or condition of the eye and/or to otherwise beneficially affect a patient's vision. The therapeutic component may be provided in a discrete region of drug delivery element, or it may be homogenously distributed throughout the drug delivery element. The therapeutic agents of the therapeutic component are typically ophthalmically acceptable, and are provided in a form that does not cause adverse reactions when the composition is placed in an eye.

In one embodiment of the present compositions, the therapeutic component may comprise one or more anti-inflammatory agents. For example, the therapeutic component of the composition may comprise at least one steroidal anti-inflammatory agent, at least one non-steroidal anti-inflammatory agent, or combinations thereof. The anti-inflammatory agent may be soluble in the ophthalmic composition or it may be insoluble in the ophthalmic composition.

Examples of poorly soluble therapeutic agents include ophthalmically acceptable therapeutic agents that have a limited solubility in a fluid, such as water, for example, at 25° C. or at 37° C. For example, the therapeutic agent may have a solubility in water at 25° C. or at 37° C. of less than 10 mg/ml.

Examples of steroidal anti-inflammatory agents include corticosteroids. In view of the above, the ophthalmic compositions may comprise a corticosteroid component. For example, the corticosteroid component may comprise one or more corticosteroids. The corticosteroid component is provided in a therapeutically effective amount, such as an amount which is effective in providing a therapeutic effect when the corticosteroid component is released from the drug delivery element in the eye. The corticosteroid component may be soluble or insoluble in the composition. The corticosteroid component may include without limitation, one or more corticosteroids selected from the group consisting of alclometasone dipropionate, amcinonide, amcinafel, amcinafide, beclamethasone, betamethasone, betamethasone dipropionate, betamethasone valerate, clobetasone propionate, chloroprednisone, clocortelone, cortisol, cortisone, cortodoxone, difluorosone diacetate, descinolone, desonide, defluprednate, dihydroxycortisone, desoximetasone, dexamethasone, deflazacort, diflorasone, diflorasone diacetate, dichlorisone, esters of betamethasone, fluazacort, flucetonide, flucloronide, fludrotisone, fluorocortisone, flumethasone, flunisolide, fluocinonide, fluocinolone, fluocinolone acetonide, flucortolone, fluperolone, fluprednisolone, fluroandrenolone acetonide, fluocinolone acetonide, flurandrenolide, fluorametholone, fluticasone propionate, hydrocortisone, hydrocortisone butyrate, hydrocortisone valerate, hydrocortamate, loteprendol, medrysone, meprednisone, methylprednisone, methylprednisolone, mometasone furoate, paramethasone, paramethasone acetate, prednisone, prednisolone, prednidone, triamcinolone acetonide, triamcinolone hexacatonide, and triamcinolone, salts thereof, derivatives thereof, and mixtures thereof. In one embodiment of the present ophthalmic composition, the corticosteroid component comprises, consists essentially of, or consists only of triamcinolone acetonide.

As used herein, the term "derivative" refers to any substance which is sufficiently structurally similar to the material which it is identified as a derivative so as to have substantially similar functionality or activity, for example, therapeutic effectiveness, as the material when the substance is used in place of the material. The functionality of any derivative disclosed herein may be determined using conventional routine methods well known to persons of ordinary skill in the art.

Other steroids which may be useful in the present compositions include, without limitation, glucocorticoids, androgenic steroids, estrogenic steroids, and non-estrogenic steroids.

In certain embodiments, the composition comprises a therapeutically effective amount of the therapeutic agent or agents before the composition is administered to an eye. In other embodiments, the composition may comprise a sub-therapeutically effective amount of the therapeutic agent before it is administered to the eye. The dissipation of the solvent when the composition is placed in the interior of the eye may be effective to form a drug delivery element comprising a relatively more concentrated amount of the therapeutic agent or agents. Thus, the drug delivery element that is formed in the interior of the eye may have a therapeutically effective amount of a therapeutic agent or agents although the initial composition had a sub-therapeutically effective amount of the agent or agents.

The therapeutic component of the compositions may be present in an amount in the range of about 1% or less to about 5% or about 10% or about 20% or about 25% or about 30% or more (w/v) of the composition. In accordance with the disclosure herein, reduced amounts of the composition may be required to be placed or injected into the interior of the eye in order to provide the same amount or more of the therapeutic agent in the interior of the eye relative to existing compositions, such as Kenalog®-40.

As used herein, a "biocompatible polymeric component" refers to a portion of the ophthalmic composition or drug delivery element which comprises one or more biocompatible polymers, such as polymers that do not cause an adverse reaction when placed in an eye, that is, the polymers should have substantially no significant or undue detrimental effect of the eye structures or tissues. The biocompatible polymer or polymers may be cross-linked together, or may be associated with each other in a matrix or network of polymers.

The biocompatible polymeric component is provided in an amount in the composition that is effective in delaying release of the therapeutic component into the interior of the eye after the composition is placed in the eye. When the therapeutic component is a corticosteroid component, the biocompatible polymeric component is effective in delaying the release of the corticosteroid component into the interior of the eye after the composition is placed in the eye.

The biocompatible polymeric component of the ophthalmic composition may be effective, after the composition is placed in the eye, to be included in a solid or gelatinous polymer matrix. In certain embodiments, the polymer matrix may be porous, for example, microporous.

The biocompatible polymeric component may comprise a water coagulable polymeric material. For example, the polymeric component may comprise one or more thermoplastic polymers or thermosetting, as disclosed in U.S. Pat. Nos. 5,077,049; 5,324,519; 5,487,897; 6,395,293; 5,702,716; 5,717,030; 5,780,044; 6,143,314; 6,261,583; 6,461,631; and 6,565,874. The polymers may comprise thermoplastic or thermosetting polymers. Thermoplastic polymers comprises a biodegradable polymer or copolymer dissolved in a solvent, such as pharmaceutically acceptable solvents and organic solvents.

In certain compositions, the polymeric component is selected from the group consisting of polylactides, polyglycolides, polycaprolactones, polyanhydrides, polyamides, polyurethanes, polyesteramides, polyorthoesters, polydioxanones, polyacetals, polyketals, polycarbonates, polyorthoesters, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, derivatives thereof and mixtures thereof.

For example, the biocompatible polymeric component of the present compositions may be selected from the group consisting of poly lactic acid, poly glycolic acid, poly lactic acid/glycolic acid (PLGA) and copolymers and mixtures thereof.

The polymers of the biocompatible polymeric component may be crosslinked or blended or used as copolymers in this invention.

As used herein, an "ophthalmically compatible solvent component" refers to a portion of the composition which comprises one or more solvents, including organic solvents which, when placed into the interior of the eye, has no substantial or undue or significant detrimental effect on the eye. Of course, such solvent should function in accordance with the present invention, as disclosed elsewhere herein.

The ophthalmically compatible solvent component of the present compositions is provided in an amount effective to solubilize the polymeric component, for example, before the composition is placed in the interior of an eye. Thus, the solvent component is effective in maintaining the therapeutic component, such as the corticosteroid component, and the polymeric component in a fluid form, such as a liquid. The solvent is preferably non-toxic and water miscible and enables the biodegradable polymer or copolymer to be provided in solution before placement in an eye.

In certain embodiments of the present compositions, the solvent component is effective in dissipating or passively or actively being removed from the composition after the composition is placed into the interior of the eye. For example, the solvent component is effective in dissipating from the liquid composition when the composition is placed in the interior of the eye. The dissipation is effective in permitting the composition to form a less fluid drug releasing composition, such as a solid, or semi-solid drug delivery implant. The drug delivery implant may be formed by a coagulation or other solidification process.

The solvent component of the present ophthalmic compositions may be non-aqueous. Alternatively or in addition, the solvent component may be water-miscible. In certain compositions, the solvent component may be organic. The solvent component may also be a liquid in the ophthalmic compositions.

The solvent component of the present compositions may be selected from the group consisting of dimethyl sulfoxide, methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, 1-dodecylazacycloheptan-2-one, and the like. Preferred solvents according to the invention include N-methyl-2-pyrrolidone, 2-pyrrolidone, dimethyl sulfoxide, ethyllactate, propylene carbonate and mixtures thereof.

In certain of the present ophthalmic compositions, the solvent component comprises dimethyl sulfoxide.

The present ophthalmic compositions may also be provided with or without a preservative component. Or, stated differently, the present compositions may include a preservative component, or may include no preservative component. Such preservative components are preferably more compatible with or friendly to the tissues in the interior of the eye into which the composition is placed than benzyl alcohol. Examples of such preservative components include, without limitation, benzalkonium, chloride, methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

The present compositions may also comprise one or more pore-forming agents. The pore-forming agents are effective in forming pores in the composition as the composition becomes less fluid or solidifies. Pores may be formed in the drug delivery element by incorporating water-soluble materials into the polymer solution. Examples of pore-forming agents include sugars, salts, and polymers, such as polymers that are not soluble in the biodegradable polymeric component or its carrier solvent. For example, the pore-forming agents may include one or more of sucrose, dextrose, sodium chloride, sodium carbonate, hydroxypropylcellulose, carboxymethylcellulose, polyethylene glycol, and polyvinylpyrollidone. The pores may have a diameter from about 3 μm to about 500 μm. For example, the pores may have a diameter from about 10 μm to about 250 μm. In certain drug delivery implants, the pores have a diameter from about 75 μm to about 150 μm.

The therapeutic component may also act as a pore forming agent for the drug delivery element. For example, dissolution of the therapeutic component from the solid or semi-solid drug delivery element may be effective in forming pores in the drug delivery element.

The present intraocular drug delivery implants which are formed in the interior of the eye are effective in releasing the therapeutic component for a prolonged period of time. For example, the therapeutic component may be released for at least about one week. In certain embodiments, the therapeutic component may be released for at least six months, such as for nine months or more. Typically, a major portion of the therapeutic component will be released within about three years from when the ophthalmic fluid composition is placed into the interior of the eye. Thus, the present compositions may be effective in providing a prolonged therapeutic effect to one or more intraocular structures of a patient. For example, the intraocular drug delivery elements that are formed in situ may provide a prolonged therapeutic effect to the retinal pigment epithelium, or other posterior ocular structure, of an eye.

The present compositions may also include one or more controlled release components, such as one or more agents were are effective in controlling the release rate of the therapeutic component from the drug delivery element. Thus, it is possible to provide pulsatile or continuous or substantially constant release profiles of the therapeutic component into the interior of the eye. In addition, the release profile may be controlled by the rate at which pores are formed in the drug delivery element. For example, a relatively higher rate of pore formation may result in a more rapid rate of release of the therapeutic component due to enhanced diffusion effects and the like.

Advantageously, it has been found that in certain situations, the drug delivery element that is formed in the interior of the eye is formed before the polymeric component of the fluid composition adheres to a surface or structure of the eye. For example, the liquid ophthalmic composition may form a drug delivery element in the interior of the eye without contacting or being dispensed onto a substrate, such as an ocular substrate. For example, the liquid composition may form an implant when the composition is injected into a cavity located in the eye, such as the posterior chamber or the anterior chamber of the eye.

In other situations, the drug delivery element may be formed upon contacting an intraocular substrate, such as a posterior intraocular substrate, of the eye. This substrate-induced formation of the drug delivery element may be effective in providing enhanced localized delivery of the therapeutic component to the eye of the patient.

In one embodiment, an ophthalmic composition suitable for forming an in situ solid implant in an animal comprises a liquid formulation of a biodegradable, bioerodible, biocompatible thermoplastic polymer that is insoluble in aqueous or body fluid, and a biocompatible organic solvent that is miscible or dispersible in aqueous or body fluid and dissolves the thermoplastic polymer. The composition is capable of coagulating or solidifying or hardening to form a solid or gelatinous macroporous matrix upon its contact with aqueous or body fluid. The matrix may be a core surrounded by a an outer layer, the core containing pores of diameters from about 1 to about 1000 microns, and the outer layer containing pores of smaller diameters than those of the core pores.

The fluid ophthalmic compositions may be manufactured by adding one or more therapeutic agents to the polymer solution to form a homogenous solution, or a suspension, or a dispersion of the agent. The polymer solution is formed by combining the biocompatible polymeric component with the solvent component. The components are mixed, blended, or otherwise processed using conventional techniques. The composition may be stored for long term use in sterile conditions, such as in sterile packages. The preparation processing should be chosen to provide the present compositions in forms which are useful for placement or injection into the interior of eyes of humans or animals. The ingredients may be mixed to disperse the therapeutic component and then may be autoclaved to sterilize the composition.

The present ophthalmic compositions may comprise other therapeutic agents instead of or in addition to the anti-inflammatory agents disclosed herein. For example, therapeutic agents may include without limitation retinoids, prostaglandins, tyrosine kinase inhibitors, adrenoreceptor agonists or antagonists, dopaminergic agonists, cholinergic agonists, carbonic anhydrase inhibitors, guanylate cyclase activators, cannabinoids, endothelin, adenosine agonists, antianagiogenic compounds, angiostatic compounds, neuroprotectants, and the like and mixtures thereof. The therapeutic component may also include, analgesics, or antipyretics; antihistamines, antibiotics, beta blockers, antineoplastic agents, immunosupressive agents, antiviral agents, antioxidants and the like and mixtures thereof.

Non-limiting examples of non-steroidal anti-inflammants, analgesics, and antipyretics, include aspirin, acetaminophen, ibuprofen, naproxen, diclofenac, etodolac, fenoprofen, indomethacin, ketoprofen, oxaprozin, piroxicam, sulindac, diflunisal, mefenamic acid, derivatives thereof, and the like and mixtures thereof.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, derivatives thereof, and the like and mixtures thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, derivatives thereof, and the like and mixtures thereof.

Examples of beta blockers include without limitation acebutolol, atenolol, labetalol, metoprolol, propranolol, derivatives thereof, and the like and mixtures thereof.

Examples of antineoplastic agents include without limitation adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, derivatives thereof, and the like and mixtures thereof.

Examples of immunosuppressive agents include without limitation cyclosporine, azathioprine, tacrolimus, derivatives thereof, and the like and mixtures thereof.

Examples of antiviral agents include without limitation interferon gamma, zidovudine, amantadine hydrochloride, ribavirin, acyclovir, valciclovir, dideoxycytidine, derivatives thereof, and the like and mixtures thereof.

Examples of antioxidant agents include without limitation ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamylcysteine, quercitin, lactoferrin, dihydrolipoic acid, citrate, Ginkgo Biloba extract, tea catechins, bilberry extract, vitamins E or esters of vitamin E, retinyl palmitate, derivatives thereof, and the like and mixtures thereof.

Other therapeutic agents include without limitation squalamine, carbonic anhydrase inhibitors, alpha agonists, prostamides, prostaglandins, antiparasitics, antifungals, derivatives thereof, and the like and mixtures thereof. Further examples include aminosterols other than squalamine that have antiangiogenic activity. Another therapeutic agent may be anecortave acetate, or similar agents or compounds which have antiangiogenic properties without substantial undesirable effects.

The therapeutic agent of the present compositions may include any and all salts, and prodrugs or precursors of the therapeutic agents, including those specifically identified herein.

The present compositions may be, and are preferably, sterile, for example, prior to being used in the eye.

Such a composition may be marketed in pre-filled syringes to facilitate administration of the composition into the interior of the eye of a patient.

The present compositions may be administered to a patient to provide a treatment to a patient. For example, the composition may be administered to a human or animal patient to treat an ocular condition or disease.

Among the diseases/conditions which can be treated or addressed in accordance with the present invention include, without limitation, the following:

MACULOPATHIES/RETINAL DEGENERATION: Non-Exudative Age Related Macular Degeneration (ARMD), Exudative Age Related Macular Degeneration (ARMD), wet macular degeneration, Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis and Uveitis Syndrome, Vogt-Koyanagi-Harada Syndrome.

VASCULAR DISEASES/EXUDATIVE DISEASES: Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angitis, Sickle Cell Retinopathy and other Hemoglobinopathies, Angioid Streaks, Familial Exudative Vitreoretinopathy, Eales Disease.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Retinitis Pigmentosa, Systemic Disorders with Accosiated Retinal Dystrophies, Congenital Stationary Night Blindness, Cone Dystrophies, Stargardt's Disease and Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum.

RETINAL TEARS/HOLES: Retinal Detachment, Macular Hole, Giant Retinal Tear.

TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

The present compositions may be placed into the interior of an eye using a syringe, a needle, a cannula, a catheter, a pressure applicator, and the like.

In one embodiment, a composition, such as the compositions disclosed herein, is administered to a posterior segment of an eye of a human or animal patient, and preferably, a living human or animal. In at least one embodiment, a composition is administered without accessing the subretinal space of the eye. For example, a method of treating a patient may include injecting the composition directly into the posterior chamber of the eye. In other embodiments, a method of treating a patient may comprise administering a composition to the patient by at least one of intravitreal injection, subconjuctival injection, sub-tenon injections, retrobulbar injection, and suprachoroidal injection. In certain situations, the method may comprise a step of applying an anesthetic to the patient, such as to the eye of the patient, before the composition is placed into the interior of the eye.

A syringe apparatus including an appropriately sized needle, for example, a 27 gauge needle or a 30 gauge needle, can be effectively used to inject the composition with the posterior segment of an eye of a human or animal. The present methods may comprise a single injection into the posterior segment of an eye or may involve repeated injections, for example over periods of time ranging from about one week or about 1 month or about 3 months to about 6 months or about 1 year or longer.

The compositions of the present invention may be placed into the eye, for example the vitreous chamber of the eye, by a variety of methods, without making an incision in the eye. The method of placement may influence the therapeutic component or drug release kinetics. The location of the implant may influence the concentration gradients of therapeutic component or drug surrounding the element, and thus influence the release rates (e.g., an element placed closer to the edge of the vitreous may result in a slower release rate).

In one embodiment, a liquid ophthalmic composition, such as the compositions disclosed herein, is administered to a posterior segment of an eye of a human or animal patient, and preferably, a living human or animal. In at least one embodiment, a composition is administered without accessing the subretinal space of the eye. For example, a method of treating a patient may include placing the composition directly into the posterior chamber of the eye. In other embodiments, a method of treating a patient may comprise administering the present composition to the patient by at least one of intravitreal injection, subconjuctival injection, sub-tenon injections, retrobulbar injection, and suprachoroidal injection. In certain situations, the compositions are administered to the interior of the eye without placing the composition in the cul-de-sac of the eye.

In another aspect of the present invention, the present compositions are used in the manufacture of a medicament that is effective to treat one or more ocular conditions, such as an ocular condition affecting the posterior segment of an eye of a patient, and including the conditions identified herein.

While this invention has been described with respect to various specific examples and embodiments, it is to be understood that the invention is not limited thereto and that it can be variously practiced within the scope of the following claims.

A number of patents have been identified herein. Each of these patents in its entirety is hereby incorporated by reference.

I claim:

1. A method of reducing the risk for cataract due to corticosteroid exposure in the eye, the method comprising placing into the interior of the eye of a human or animal an ophthalmic composition comprising a corticosteroid component present in a therapeutically effective amount, carboxymethylcellulose, a biocompatible polymeric component, and an ophthalmically compatible solvent component;
   wherein the ophthalmic composition is administered as a liquid and becomes a semi-solid or gelatinous polymer matrix after placement in the interior of the eye;
   wherein the ophthalmic composition is placed into the interior of the eye by suprachoroidal injection;
   wherein the biocompatible polymeric component is selected from the group consisting of polylactides, polyglycolides, polycaprolactornes, polyanhydrides, polyamides, polyurethanes, polyesteramides, polyorthoesters, polydioxanones, polyacetals, polyketals, polycarbonates, polyorthoesters, polyphosphazenes, polyhydroxybutyrates, polyhydroxyvalerates, polyalkylene oxalates, polyalkyene succinates, poly(malic acid), poly(amino acids), poly(methyl vinyl ether), poly(maleic anhydride), polylactic acid, polyglycolic acid, polylactic acid/glycolic acid, chitin, chitosan, copolymers thereof, combinations thereof and mixtures thereof; and
   wherein the ophthalmically compatible solvent component is selected from the group consisting of dimethyl sulfoxide, methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, 1-dodecylazacycloheptan-2-one, combinations thereof and mixtures thereof.

2. The method of claim 1, wherein the corticosteroid is selected from the group consisting of alclometasone dipropionate, amcinonide, amcinafel, amcinafide, beclomethasone, betamethasone, betamethasone dipropionate, betamethasone valerate, clobetasone propionate, chloroprednisone, clocortelone, cortisol, cortisone, cortodoxone, difluorosone diacetate, descinolone, desonide, dehluprednate, dihydroxycortisone, desoximetasone, dexamethasone, deflazacort, diflorasone, diflorasone diacetate, dichlorisone, esters of betamethasone, fluazacort, flucetonide, flucloronide, fludrotisone, fluorocortisone, flumethasone, flunisolide, fluocinonide, cluocinolone, fluocinolone acetonide, flucortolone, fluperolone, fluprednisolone, fluroandrenolone acetonide, fluocinolone acetonide, flurandrenolide, fluorametholone, fluticasone propionate, hydrocortisone, valerate, hydrocortamate, loteprendol, medrysone, meprednisone, methylprednisone, methylprednisolone, mometasone furoate, paramethasone, paramethasone acetate, prednisone, prednisolone, prednidone, triamcinolone acetonide, triamcinolone hexacatonide, triamcinolone, and salts thereof.

3. The method of claim 2, wherein the corticosteroid is beclomethasone and salts thereof.

4. A method of reducing the risk for cataract due to beclomethasone exposure in the eye, the method comprising placing into the interior of the eye of a human or animal an ophthalmic composition comprising beclomethasone present in a therapeutically effective amount, carboxymethylcellulose, a biocompatible polymeric component in an amount effective to delay release of the beclomethasone into the interior of the eye after the composition is placed in the eye, and an ophthalmically compatible solvent component in an amount effective to solubilize the polymeric component; wherein the ophthalmic composition is administered as a liquid and wherein the ophthalmic composition is placed into the interior of the eye by suprachoroidal injection.

5. The method of claim 4, wherein the biocompatible polymeric component is selected from the group consisting of polylactides, polyglycolides, polycaprolactornes, polyanhydrides, polyamides, polyurethanes, polyesteramides, polyorthoesters, polydioxanones, polyacetals, polyketals, polycarbonates, polyorthoesters, polyphosphazenes, polyhydroxybutyrates, polyhydroxyvalerates, polyalkylene oxalates, polyalkyene succinates, poly(malic acid), poly(amino acids), poly(methyl vinyl ether), poly(maleic anhydride), polylactic acid, polyglycolic acid, polylactic acid/glycolic acid, chitin, chitosan, copolymers thereof, combinations thereof and mixtures thereof.

6. The method of claim 4, wherein the ophthalmically compatible solvent component is selected from the group consisting of dimethyl sulfoxide, methyl-2-pyrrolidone, 2-pyrrolidone, $C_2$ to $C_6$ alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, 1-dodecylazacycloheptan-2-one, combinations thereof and mixtures thereof.

* * * * *